US008633827B2

(12) United States Patent
Lakshminarayanan

(10) Patent No.: US 8,633,827 B2
(45) Date of Patent: Jan. 21, 2014

(54) PATIENT TABLE SYSTEM FOR MEDICAL SYSTEM FOR MEDICAL APPLICATIONS AND ASSOCIATED MEDICAL IMAGING DEVICE

(75) Inventor: Ramanan Lakshminarayanan, Karnataka (IN)

(73) Assignee: General Electric Company, Schenectady, NY (US)

( * ) Notice: Subject to any disclaimer, the term of this patent is extended or adjusted under 35 U.S.C. 154(b) by 192 days.

(21) Appl. No.: 13/165,900

(22) Filed: Jun. 22, 2011

(65) Prior Publication Data
US 2011/0309944 A1 Dec. 22, 2011

(30) Foreign Application Priority Data

Jun. 22, 2010 (EP) .................................... 10166926

(51) Int. Cl.
G08B 21/00 (2006.01)
G08B 5/22 (2006.01)
G08B 17/12 (2006.01)
A47B 71/00 (2006.01)

(52) U.S. Cl.
USPC ........ 340/665; 340/666; 340/286.7; 340/600; 5/600

(58) Field of Classification Search
USPC .......... 340/665, 600, 667, 601, 286.07; 5/600
See application file for complete search history.

(56) References Cited

U.S. PATENT DOCUMENTS

| 4,146,793 | A | 3/1979 | Bergstrom et al. |
| 4,738,267 | A | 4/1988 | Lazorthes et al. |
| 5,077,780 | A | 12/1991 | Lee, Jr. |
| 5,741,606 | A * | 4/1998 | Mayer et al. ................ 429/53 |
| D408,537 | S | 4/1999 | Stickley et al. |
| 6,023,800 | A | 2/2000 | Stickley |
| 6,499,158 | B1 | 12/2002 | Easterling |
| 6,986,179 | B2 | 1/2006 | Varadharajulu et al. |
| 7,167,739 | B2 | 1/2007 | Van De Rijdt et al. |
| 7,264,396 | B2 | 9/2007 | Jahrling |
| 7,834,768 | B2 * | 11/2010 | Dixon et al. ................ 340/573.1 |
| 7,978,084 | B2 * | 7/2011 | Dixon et al. ................ 340/573.1 |
| 8,108,957 | B2 * | 2/2012 | Richards et al. ................ 5/600 |
| 2003/0223882 | A1 * | 12/2003 | Greene, Jr. .................... 417/212 |
| 2004/0172757 | A1 | 9/2004 | Somasundaram |
| 2005/0031080 | A1 | 2/2005 | Klingenbeck-Regn |
| 2006/0173273 | A1 | 8/2006 | Boese |
| 2006/0174412 | A1 | 8/2006 | Hornig |
| 2007/0258896 | A1 * | 11/2007 | Nachaliel ........................ 424/9.1 |
| 2008/0060127 | A1 | 3/2008 | Lakshminarayanan |
| 2008/0201849 | A1 | 8/2008 | Van Es et al. |
| 2011/0168903 | A1 * | 7/2011 | Kyele et al. ................. 250/370.1 |
| 2011/0302720 | A1 * | 12/2011 | Yakam et al. ...................... 5/710 |

* cited by examiner

FOREIGN PATENT DOCUMENTS

| JP | 6237926 A | 8/1994 | |
| JP | 11192222 A | * 7/1999 | ............... A61B 6/04 |

OTHER PUBLICATIONS

Author Anonymous "Method of Testing Patient Handling Table Tops" Defensive Publication IP.Com No. IPCOM000193362D, Feb. 18, 2010.

Primary Examiner — George Bugg
Assistant Examiner — Munear Akki
(74) Attorney, Agent, or Firm — Global Patent Operation; Marc A. Vivenzio

(57) ABSTRACT

A patient table system for medical applications is provided. The table system comprises: a table top; at least one sensor configured to measure information representative of a pressure exerted by a patient on the table top when the patient is in a lying position; and a safety detector configured to compare the measured information with reference data of the table top mechanical resistance and to provide an alert depending on the result of the comparison.

14 Claims, 3 Drawing Sheets

PATIENT TABLE SYSTEM FOR MEDICAL SYSTEM FOR MEDICAL APPLICATIONS AND ASSOCIATED MEDICAL IMAGING DEVICE

BACKGROUND OF THE INVENTION

1. Field of the Invention

Embodiments of the present invention generally relate to a patient table system for medical applications comprising a table top and more particularly to a patient table system which ensures safety of patients lying on the table top.

Embodiments of the present invention are also related to an imaging medical system comprising a patient table system and to a method for preventing the breakage of the table top in a patient table system.

2. Description of the Prior Art

In most medical imaging systems, such as MRI, CT scan, or X-ray imaging devices, a patient 4 is asked by a medical practitioner to lie on a table top 2 of a patient table system 1, as depicted in FIG. 1. While lying on said table top 2, the patient undergoes medical imaging analysis.

The patient table system 1 generally comprises means for moving the table top 2, such as elevation, rotation, tilting, longitudinal, and lateral moving means.

Usually, the table tops are stiff plate-like members, in a composite material.

In general, the table top 2 is supported by a table base 17 at one end, wherein the table base 17 is a supporting unit underneath the table top 2, while the other end of the table top 2 is a cantilever zone 12 which is not supported by any mechanical structure.

The cantilever zone 12 is not supported by any mechanical structure in order to avoid the creation of image artifacts. The cantilever zone 12 is thus structurally weaker than the rest of the table top.

When the patient lies on the table top 2, mainly on the cantilever zone 12, he exerts a pressure on the table top 2 due to his weight. Table tops are in general designed to resist to predefined mechanical constraints.

However, it can occur that the table top 2 breaks under the weight of the patient, which can lead to the fall of the patient and to patient injuries.

In order to ensure the patient safety in all circumstances, it would be preferable to avoid these situations.

Hence, there is a need for a reliable and flexible solution than can prevent the patient from breaking the table top in medical imaging systems.

SUMMARY OF THE INVENTION

In one embodiment, a patient table system for medical applications is provided. The table system comprises: a table top; at least one sensor configured to measure information representative of a pressure exerted by a patient on the table top when the patient is in a lying position; and a safety detector configured to compare the measured information with reference data of the table top mechanical resistance and to provide an alert depending on the result of the comparison.

In an alternate embodiment, a medical imaging system is provided. The medical imaging system comprises a patient table system, the patient table system comprising: a table top; at least one sensor configured to measure information representative of a pressure exerted by a patient on the table top when the patient is in a lying position; and a safety detector configured to compare the measured information with reference data of the table top mechanical resistance and to provide an alert depending on the result of the comparison.

In an alternate embodiment, a method for preventing the breakage of a table top in a patient table system for medical applications is provided. The method comprises: measuring information representative of a pressure exerted by a patient on the table top when the patient is in a lying position with at least one sensor of the patient table system; comparing the measured information with reference data of the table top mechanical resistance with a safety detector; and providing an alert with the safety detector depending on the result of the comparison.

BRIEF DESCRIPTION OF THE DRAWINGS

These and other advantages of the embodiments of the present invention will be more apparent from the following description in view of the drawings, wherein.

DETAILED DESCRIPTION OF THE INVENTION

Figure 1:
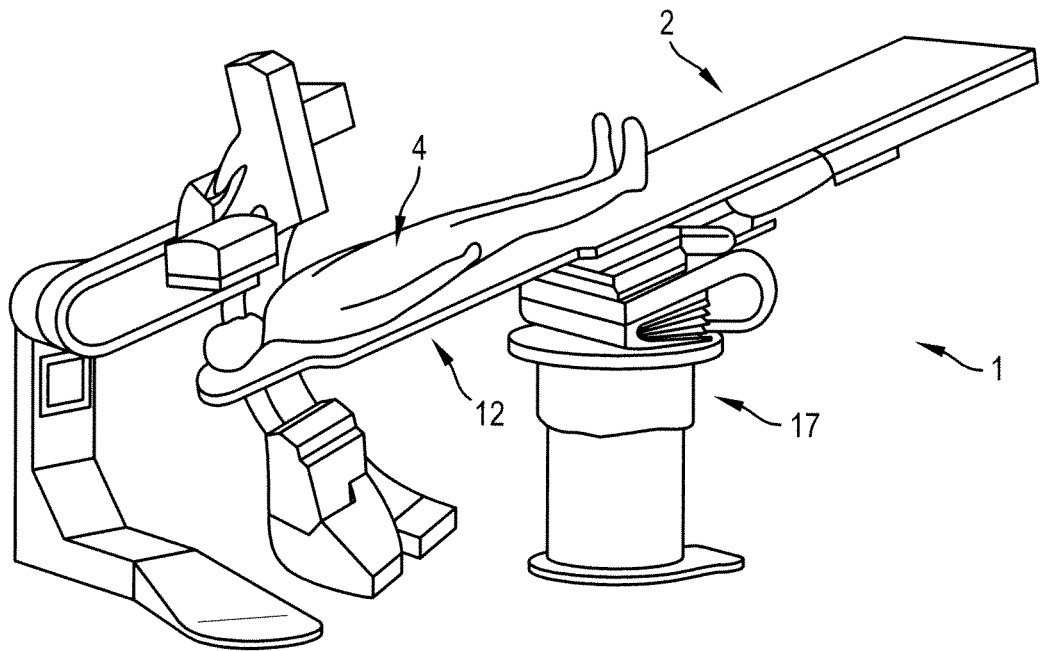
FIG. 1 is a schematic representation of a prior art patient table system in a medical imaging system.
Figure 2:
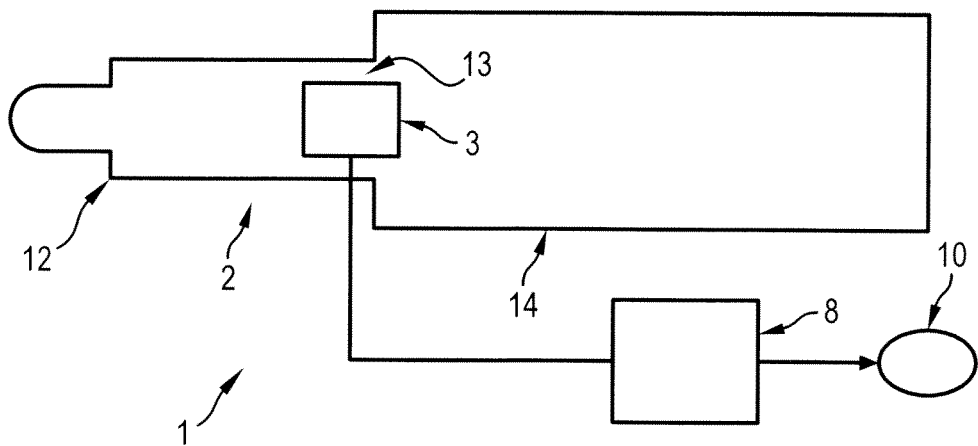
FIG. 2 is a schematic representation of a patient table system according to one embodiment of the invention.

A patient table system 1 according to one embodiment of the invention is schematically depicted in FIG. 2, in an upper view. The patient table system 1 is suitable for supporting a patient in medical applications.

The patient table system comprises a table top 2 for supporting a patient in lying position. In addition, the patient table system 1 comprises at least a sensor 3, configured to measure information representative of the pressure exerted by the patient on the table top 2 in a lying position. As it will be apparent from the different embodiments of the invention, various sensors can be used. Of course, multiple sensors 3 can be used. In the present description, the expression "the sensor" shall not be limited to the use of a unique sensor.

The patient table system 1 further comprises a safety detector 8, configured to compare the measured information with reference data of the table top 2 mechanical resistance, and to provide an alert 10 depending on the result of said comparison.

When a patient lies on the table top 2, he exerts a pressure on the table top 2 due to his weight.

Figure 3:
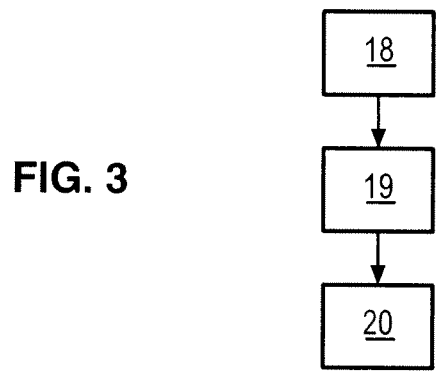
FIG. 3 is a representation of a method according to one embodiment of the invention.

One embodiment of the method for preventing the breakage of the table top 2 is depicted in FIG. 3.

The sensor 3 measures (step 18) information representative of the pressure exerted by the patient on the table top 2 in a lying position. The safety detector 8 compares (step 19) the measured information with reference data corresponding to the mechanical resistance of the table top 2.

When the safety detector 8 detects that the measured information reaches or is beyond reference data corresponding to the mechanical resistance of the table top 2, the safety detector 8 provides an alarm 10 (step 20).

Depending on the result of the comparison between the measured information and reference data, the safety detector 8 will provide an alarm, or not. This alarm can be a visual and/or audio indication which alerts the medical staff of the overweight caused by the patient on the table top 2, and of the risk of breakage of the table top 2.

Thus, the medical practitioner can ask the patient to leave the table top 2, or to adapt his lying position, which avoids the breakage of the table top 2 and patient injury.

The reference data is computed through simulation and/or experimental tests and model the table top mechanical resistance, that is to say the maximum pressure that can be supported by the table top in operation. The reference data of the table top mechanical resistance is not limited to pressure data, and can be computed in terms of load, force, displacement or stretch data. These parameters are all representative of the pressure exerted by a patient on the table top 2, due to his weight, which can be supported by said table top 2 in operation.

The reference data can be based on a worst case scenario, or multiple worst case scenarios, which correspond to the maximum load or pressure that can be supported by the table top 2 in operation for a given design and position of the table top 2.

In one embodiment, a computer model of the table top 2 is built. Various factors and limitations are considered in the computer model. This includes for instance the various material characteristics of the table. The model also includes the different positions and movements of the table top in operation: lowering of the table, raising of the table, tilting of the table, etc.

The model can be built using finite element methods. This model is used for mathematical calculations to evaluate various loading conditions of the table. The simulated loading can be for instance as per the specifications and regulatory needs of the patient weight.

The results obtained from mathematical evaluations performed on the computed model may be tabulated to identify worst case scenario. The worst case scenario can be validated through experimental tests, such as strain gauging tests. The worst case scenario corresponds in general to an information representative of the maximum pressure that can be supported by the table top 2.

The safety detector 8 is in general configured to detect that the worst case scenario which can be supported by the table top 2 is reached or nearly reached, and to raise an alarm 10.

Various sensors 3 can be used to measure information representative of the pressure exerted by the patient on the table top 2 in a lying position.

In one embodiment, the sensor 3 comprises at least a pressure sensor, configured to measure the pressure exerted by the patient on the table top 2. In this embodiment, the information representative of the pressure exerted by the patient on the table top 2 in a lying position is the pressure itself.

In another embodiment, the sensor 3 comprises at least a force sensor, configured to measure a force exerted by the patient on the table top. It is clear that the force exerted by the patient on the table top 2 is representative of the pressure exerted by said patient on said table top 2.

In another embodiment, the sensor 3 comprises at least a displacement sensor, configured to measure a displacement of the table top 2 caused by the patient. It is clear that the displacement of the table top 2 is representative of the pressure exerted by the patient on the table top 2.

The choice of the sensor technology is not limited and any technology known by a person skilled in the art and adapted to the patient table system 1 could be used. This includes, but is not limited to: strain gauges, LVDT (Linear Variable Differential Transformer), laser displacement or deflection sensors, load cells, piezoelectric sensors, and pressure transducers. A combination of different types of sensors may also be used.

In a particular embodiment, the sensor is transparent to X-rays, in order to avoid image artifacts. This type of sensor is made of a non-magnetic and X-ray transparent body. One example of such a sensor is described in U.S. Pat. No. 4,738,267.

The sensor can communicate with the safety detector 8 through a wired channel, or a wireless channel. The safety detector 8 comprises in general a processor associated to software, and can be a dedicated unit or can be integrated in the processing unit of the medical imaging system.

In one embodiment, the sensor consists of one or more telltale devices configured to break when the pressure exerted by the patient on the table top 2 reaches or goes beyond a predetermined threshold.

In this embodiment, the table top 2 is clearly designated as out of use when the telltale device breaks, even if its external appearance appears to be satisfactory.

Various breaking telltale devices can be used, such as mechanical telltale devices or electrical telltale devices. Mechanical telltale device includes for instance a pin designed to resist to a predestined mechanical constraint.

In one embodiment, the telltale device is made of metallic wires, in which an electric current is flowing. When the pressure exerted by the patient on the table top 2 reaches or goes beyond a predetermined threshold, the safety detector 8 detects that an electric circuit comprising said metallic wires is in open loop, which means that the table top 2 is out of use. One advantage of the use of metallic wires is that they are too small to be visible in X-rays imaging, which avoids the creation of images artifacts.

Other embodiments of the telltale device include the use of glass wires with optical continuity.

One advantage of the use of telltale device is the low cost of this solution.

In particular, multiple telltale devices can be used, either in series or in parallel. The position of the telltale devices can be chosen to detect particular breakage. The telltale devices can be positioned, for instance, in various locations or zones of the table top, on the table top, under the table top, or in various components of the patient table system (assembling means such as assembling glue, foam of the patient table system which is interposed between the patient and the table top, composite material of the table top, etc.). The multiplication of telltale devices allows an immediate and precise identification of the zones of the table top and/or the components of the patient table system which are broken.

The threshold can coincide with a property which is representative of the mechanical resistance of the table top, such as its elastic limit, or any adapted property.

The threshold can coincide with a property which is representative of the mechanical resistance of one component of the patient table system. As already underlined, the patient table system comprises several components. This includes for instance the carbone composite of the table top and/or the assembling glue and/or the foam which is interposed between the patient and the table top. The threshold of the telltale device is thus designed depending on the desired location of said telltale device.

Figure 4:
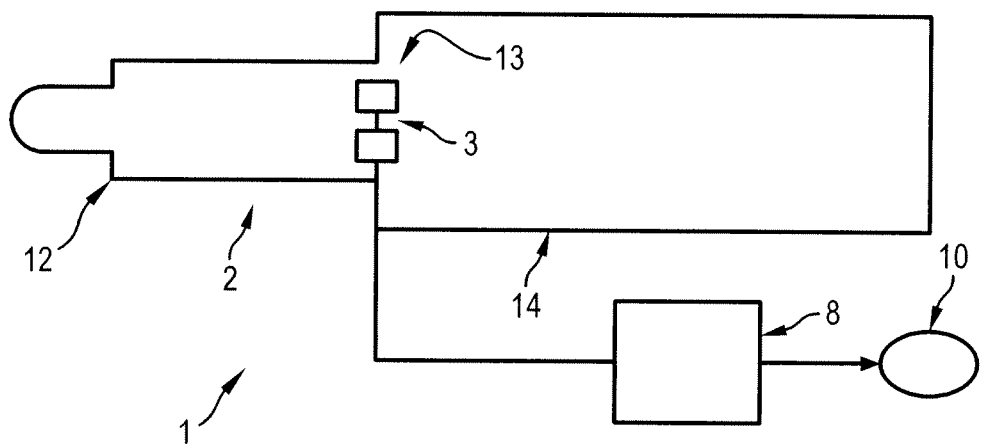
FIG. 4 is a representation of a patient table system according to one embodiment of the invention.
Figure 5:
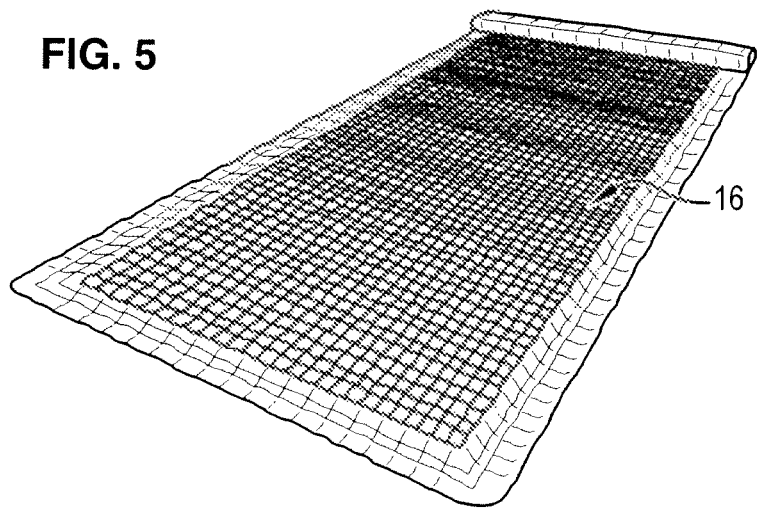
FIG. 5 is a representation of a sensor array which can be used in the patient table system according to one embodiment of the invention.

This solution allows a simple, efficient and low cost detection of the table top breakage In one embodiment, and as represented in FIG. 4, the table top 2 comprises at one end a cantilever zone 12, which is not supported by any mechanical structure. A zone 14 of the table top 2 adjacent to said cantilever zone 12 is disposed at the other end of the table top 2. This zone 14 is supported by a mechanical structure, such as a table base, which is not represented in FIG. 4.

In this embodiment, the sensor 3 is disposed at the interface 13 between the cantilever zone 12 and the zone 14 of the table top 2 adjacent to said cantilever zone 12.

Indeed, when a breakage of the table top 2 occurs, it is likely to occur at this interface 13, which is subject to high mechanical constraints.

Thus, by positioning the sensor 3 at this interface 13, the detection of a breakage of the table top 2 by the sensor 3 is optimal. The interface 13 is a critical point to monitor.

The sensor 3 can be placed on the table top 2, under the table top 2, or in the table top 2 itself.

In a particular embodiment, the patient table system 1 comprises a mattress of sensors 16 covering at least one side of the table top 2, or a portion of at least one side of said table top 2. For example, the mattress of sensors 16 can be positioned on the top and/or the bottom of the table top 2. The mattress of sensors 16 is to be understood as a sensor array, comprising multiple sensors, said sensors being disposed according to a regular or irregular grid. It is possible to integrate the mattress of sensors 16 inside the table top 2.

The mattress of sensors 16 can be chosen so as to be transparent to X-rays, in order to avoid image artifacts.

The mattress of sensors 16 comprises a sensor array, which can include pressure sensors. This allows the multiplication of sensing points. The sensing points are disposed on a grid on the mattress of sensors 16. In this embodiment, the pressure distribution exerted by the patient on the table top can be measured on the whole table top, or at least on a large zone of said table top.

In one embodiment, the table top 2 is covered by a non-rigid mattress to support the patient 4 in a lying position, such as a foam mattress. This non-rigid mattress improves the patient comfort when he is lying on the table top 2, made of a stiff plate-like member.

The mattress of sensors 16 can be disposed on the top and/or on the bottom of said non-rigid mattress, or even inside said non-rigid mattress, in order to measure information on the pressure exerted by the patient on the whole table top 2. The measure is thus not limited to specific points as in the other embodiments, but is performed on a large zone.

This allows the measure of a pressure distribution, which can be compared with reference data of the patient pressure distribution on the table top 2.

The reference data of the patient pressure distribution can correspond to acceptable pressure distribution, which are below or equal to the mechanical resistance of the table top 2, in its different positions and design.

The safety detector 8 can thus detect a risk of breakage of the table top 2. With this configuration, an unequal mass distribution of the patient lying on the table top 2 can be detected. Indeed, in some cases, the position of the patient might not be well balanced on the table top 2, which increases the risks of the table top breakage.

Figure 6A:
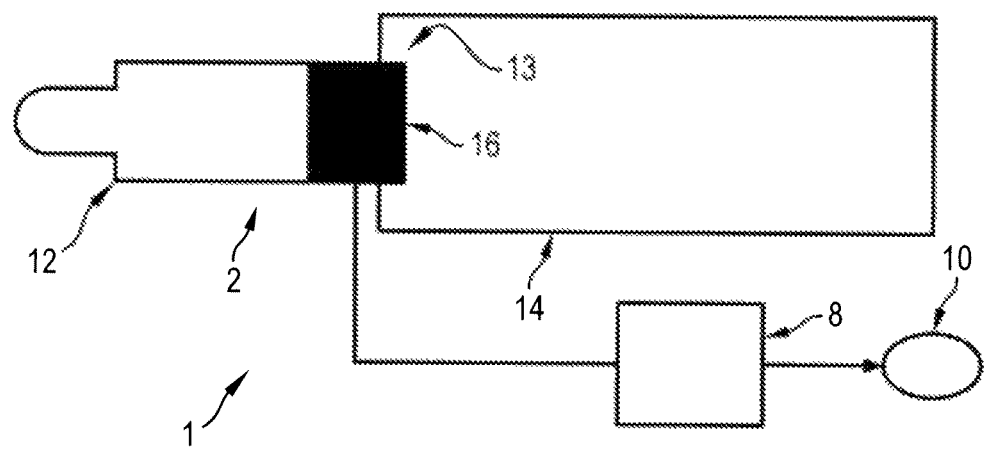
FIGS. 6A and 6B represent a patient table system according to one embodiment of the invention, in an upper and side view respectively.
Figure 6B:
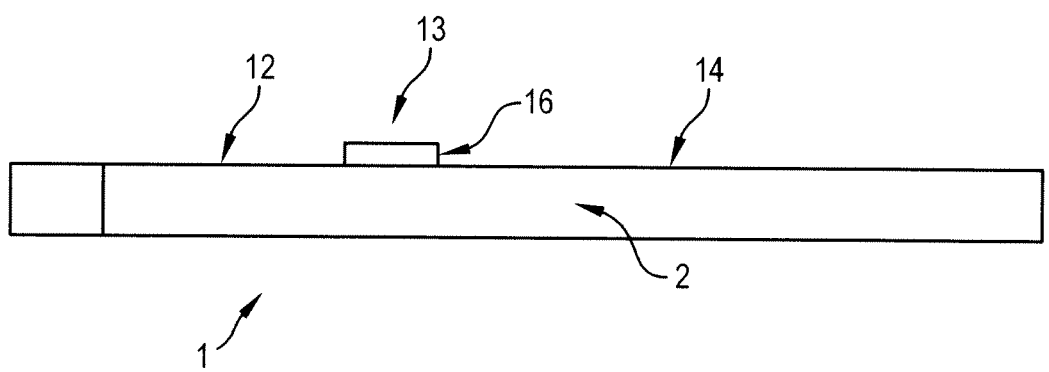

In one embodiment, depicted in FIGS. 6A and 6B, the patient table system 1 comprises a mattress of sensors 16 at the interface 13 between the cantilever zone 12 and the zone 14 of the table top 2 adjacent to said cantilever zone 12, said zone 14 being supported by a mechanical structure. This allows a precise measure of the pressure at the interface 13 between the cantilever zone 12 and the zone 14 of the table which is supported by a mechanical structure. In this embodiment, the mattress of sensors 16 is restricted to the region of interest consisting in the interface 13. Thus, the prevention of the table top 2 breakage is improved.

The patient table system 1 can be integrated to a large variety of medical imaging systems including, but not limited to an MRI device, a CT scan device, an X-ray imaging device, and angiography. This versatility is one of the system advantages.

The patient table system 1 provides several additional advantages. This system ensures the safety of the patient during the medical imaging phase.

In addition, the system can alert the medical practitioner in real time when a risk of breakage is detected.

It thus allows the protection of the components of the medical imaging system and increases their lifetime.

In the embodiment using the mattress of sensors, it is possible to get real time information of the patient profile pressure distribution exerted on the table top.

The system can measure in real time the weight of the patient and can be configured so as to correlate the measured weight with the patient data entered in the system or in the medical imaging system (for instance by an operator, such as a medical practitioner, which can enter the weight of the patient).

It is thus possible to crosscheck that the right patient is lying on the table top in the medical imaging system. The patient table system thus ensures data integrity.

The patient table system 1 provides a simple and flexible solution to enhance patient safety in medical imaging systems.

What is claimed is:

1. A patient table system for medical applications comprising:
   a table top;
   at least one sensor configured to measure information representative of a pressure exerted by a patient on the table top when the patient is in a lying position on the table top; and
   a safety detector configured to compare the measured information with reference data of the table top mechanical resistance and to provide, depending on the result of the comparison, an alert of a risk of breakage of the table top.

2. The patient table system of claim 1, wherein the at least one sensor comprises at least one of a pressure sensor configured to measure a pressure exerted by the patient on the table top, a force sensor configured to measure a force exerted by the patient on the table top and a displacement sensor configured to measure a displacement of the table top caused by the patient.

3. The patient table system of claim 1, wherein the sensor is transparent to X-rays.

4. The patient table system of claim 1, wherein the table top comprises a cantilever zone and a zone adjacent to the cantilever zone, and wherein the sensor is disposed at the interface between the cantilever zone and the zone adjacent to the cantilever zone.

5. The patient table system of claim 1, comprising a mattress of sensors covering at least one side of the table top.

6. The patient table system of claim 4, comprising a mattress of sensors disposed at the interface between the cantilever zone and the zone adjacent to the cantilever zone.

7. The patient table system of claim 1, wherein the table top is covered by a non-rigid mattress, and wherein a mattress of sensors is disposed on the top and/or the bottom of the non-rigid mattress.

8. The patient table system of claim 1, wherein the safety detector is configured to compare the measured information representative of the pressure exerted by the patient on the table top with at least a worst case scenario, wherein the worst case scenario corresponds to information representative of a maximum pressure that can be supported by the table top.

9. A patient table system for medical applications comprising:
- a table top;
- at least one sensor configured to measure information representative of a pressure exerted by a patient on the table top when the patient is in a lying position on the table top, the at least one sensor comprising at least one telltale device configured to break when a pressure exerted by the patient on the table top reaches or goes beyond a predetermined threshold representative of the mechanical resistance of the table top or of one component of the patient table system; and
- a safety detector configured to compare the measured information with reference data of the table top mechanical resistance and to provide an alert depending on the result of the comparison.

10. The patient table system of claim 1, wherein the patient table system is part of or integrated into a medical imaging system.

11. A method for preventing the breakage of a table top in a patient table system for medical applications, the method comprising:
- measuring information representative of a pressure exerted by a patient on the table top when the patient is in a lying position on the table top with at least one sensor of the patient table system;
- comparing the measured information with reference data of the table top mechanical resistance with a safety detector; and
- providing an alert with the safety detector and, depending on the result of the comparison, alerting of a risk of breakage of the table top.

12. The patient table system of claim 1, wherein the alert is provided in real time.

13. The patient table system of claim 9, wherein the alert is provided in real time.

14. The method of claim 11, wherein the alerting occurs in real time.

* * * * *